United States Patent
LeBlanc et al.

(10) Patent No.: US 10,261,243 B2
(45) Date of Patent: Apr. 16, 2019

(54) FIBER OPTIC SENSING USING SOLUBLE LAYERS

(71) Applicant: Halliburton Energy Services, Inc., Houston, TX (US)

(72) Inventors: Michel LeBlanc, Houston, TX (US); Neal G. Skinner, Lewisville, TX (US); William C. Pearl, Jr., Houston, TX (US); Megan R. Pearl, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/517,071

(22) PCT Filed: Nov. 24, 2015

(86) PCT No.: PCT/US2015/062262
§ 371 (c)(1),
(2) Date: Apr. 5, 2017

(87) PCT Pub. No.: WO2017/091203
PCT Pub. Date: Jun. 1, 2017

(65) Prior Publication Data
US 2018/0252555 A1 Sep. 6, 2018

(51) Int. Cl.
*G02B 6/02* (2006.01)
*G01N 21/77* (2006.01)
(Continued)

(52) U.S. Cl.
CPC .......... *G02B 6/02104* (2013.01); *E21B 47/00* (2013.01); *E21B 47/10* (2013.01);
(Continued)

(58) Field of Classification Search
None
See application file for complete search history.

(56) References Cited

U.S. PATENT DOCUMENTS 5,493,113 A * 2/1996 Dunphy ............. G01D 5/35383
250/227.14
5,828,798 A * 10/1998 Hopenfeld ......... G01N 21/7703
385/12
(Continued)

FOREIGN PATENT DOCUMENTS

EP 2565630 A1 * 3/2013
JP 04-148836 A1 5/1992

OTHER PUBLICATIONS

International Search Report and The Written Opinion of the International Search Authority, or the Declaration, dated Oct. 26, 2016, PCT/US2015/062262, 21 pages, ISA/KR.
(Continued)

*Primary Examiner* — Michael Stahl
(74) *Attorney, Agent, or Firm* — Haynes and Boone, LLP (57) ABSTRACT

Optical sensors having one or more soluble coatings thereon are used to detect the presence of a degrading fluid. In a generalized embodiment, the fiber optic sensor includes a fiber optic cable having two strain sensor positioned therein. A soluble layer is positioned over one of the strain sensor. Due to the presence of the soluble layer, the covered strain sensor optically responds differently than the other strain sensor to changes in pressure, strain and temperature. In the presence of a degrading fluid, the soluble layer degrades and ultimately dissolves, thereby changing the optical response of the previously covered strain sensor. When the soluble layer is dissolved, the strain induced by the soluble layer relaxes, thus causing a wavelength shift in the signal of the grating. By monitoring the wavelength shifts of both strain sensors, the fiber optic sensor acts as a detector for the presence of the degrading fluid.

31 Claims, 6 Drawing Sheets

(51) Int. Cl.
*E21B 47/00* (2012.01)
*E21B 47/10* (2012.01)
*G01D 5/353* (2006.01)
*G02B 6/44* (2006.01)
*G02B 6/00* (2006.01)

(52) U.S. Cl.
CPC ......... *E21B 47/102* (2013.01); *G01D 5/3537* (2013.01); *G01N 21/774* (2013.01); *G02B 6/00* (2013.01); *G02B 6/02076* (2013.01); *G02B 6/4428* (2013.01)

(56) References Cited

U.S. PATENT DOCUMENTS

| | | | | |
|---|---|---|---|---|
| 6,144,026 | A * | 11/2000 | Udd | G01D 5/35383 250/227.14 |
| 7,336,862 | B1 | 2/2008 | Xai et al. | |
| 8,831,388 | B2 | 9/2014 | Boersma et al. | |
| 2003/0118297 | A1* | 6/2003 | Dunphy | G01M 11/083 385/102 |
| 2004/0184734 | A1 | 9/2004 | Mihailov et al. | |
| 2006/0165344 | A1* | 7/2006 | Mendez | E21B 47/06 385/13 |
| 2007/0019898 | A1* | 1/2007 | Chimenti | G01L 1/246 385/12 |
| 2009/0156942 | A1* | 6/2009 | Phillips | A61B 5/0059 600/478 |
| 2011/0149293 | A1 | 6/2011 | Dorner | |
| 2015/0049981 | A1 | 2/2015 | Balasubramaniam et al. | |
| 2015/0377765 | A1* | 12/2015 | Chilukuri | G01N 17/04 356/73.1 |
| 2017/0138862 | A1* | 5/2017 | Boersma | G01N 21/774 |

OTHER PUBLICATIONS

Boersma, et al., "Fiber Bragg Distributed Chemical Sensor," *IEEE*, Oct. 28, 2011.

* cited by examiner

FIBER OPTIC SENSING USING SOLUBLE LAYERS

PRIORITY

The present application is a U.S. National Stage patent application of International Patent Application No. PCT/US2015/062262, filed on Nov. 24, 2015, the benefit of which is claimed and the disclosure of which is incorporated herein by reference in its entirety.

FIELD OF THE DISCLOSURE

The present disclosure relates generally to optical sensors and, more specifically, to an optical sensor having a soluble coating used to detect the presence of one or more fluids.

BACKGROUND

In the field of hydrocarbon recovery, there are many situations in which it would be desirable to determine the presence of certain fluids at a location or several locations in the downhole environment. For example, in cementing operations, it may be desirable to determine when water is present in order to maintain the integrity of the cement layer. In steam flooding operations or other stimulation operations, it would be desirable to determine the presence of a treatment fluid. In production operations, it would be desirable to determine the presence of hydrocarbon, water, or acid in the well. Once the presence of these fluids is known, remedial or other downhole operations may be conducted accordingly.

DESCRIPTION OF ILLUSTRATIVE EMBODIMENTS

Illustrative embodiments and related methods of the present disclosure are described below as they might be employed in an optical sensor having a soluble layer thereon used to detect the presence of a fluid. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

As described herein, illustrative embodiments of the present disclosure are directed to optical sensors having one or more soluble coatings thereon used to detect the presence of a particular fluid (e.g., type of acid) or class of fluids (e.g., acid, hydrocarbon, water). In a generalized embodiment, the fiber optic sensor includes a fiber optic cable having two strain sensors positioned therein. Although the strain sensors may take a variety of forms, the present disclosure will focus on Bragg gratings. In this illustrative embodiment, the Bragg gratings are axially separated along the fiber optic cable a defined distance. A soluble layer is positioned over one of the Bragg gratings. Due to the presence of the soluble layer, the covered Bragg grating optically responds differently than the other Bragg grating to chances in pressure, strain and temperature. In the presence of a degrading fluid, the soluble layer degrades and ultimately dissolves, thereby changing the optical response of the previously covered Bragg grating. When the soluble layer is completely dissolved, the strain induced by the soluble layer is relaxed, thus shifting the signal wavelength of the previously covered grating. By measuring the wavelength shifts of both Bragg gratings, the fiber optic sensor acts as a detector for the presence of the degrading fluid. Moreover, a variety of methods for fabricating and using the fiber optic sensors are described herein.

Figure 1:
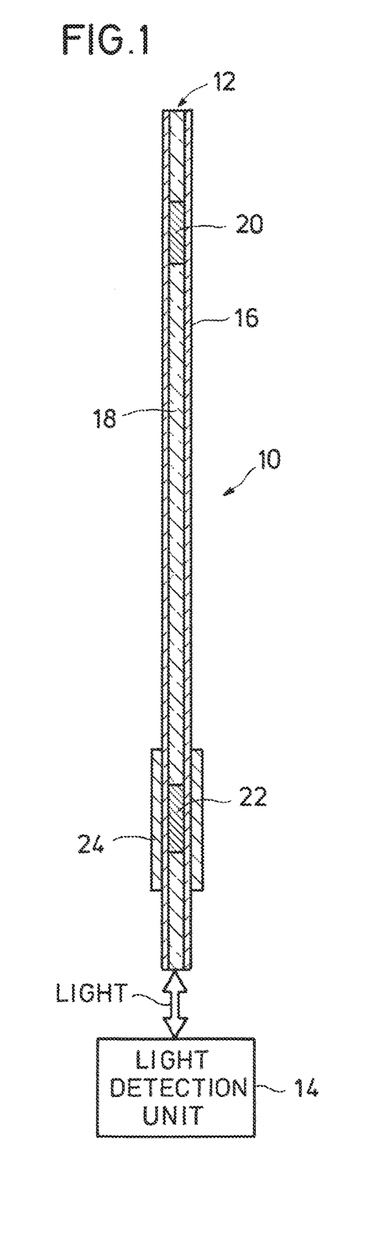
FIG. 1 is a sectional depiction of a fiber optic sensor, according to certain illustrative embodiments of the present disclosure.

FIG. 1 is a sectional depiction of a fiber optic sensor, according to certain illustrative embodiments of the present disclosure. Fiber optic sensor 10 includes a cable 12 that optically couples to a light detection unit 14. Fiber optic cable 12 is cladded as understood in the art, and includes a protecting coating 16, such as, for example, a polyimide coating. Protecting coating 16 protects optical fiber 18 against surface deterioration, which would otherwise lead to reduced tensile strength of the optical fiber, and possible attenuation of the optical signal.

Fiber optic sensor includes two strain sensors. In this example, the strain sensors are Bragg gratings. A first reference Bragg grating 20 is positioned along core 18. A second Bragg grating 22 is positioned along core 18 and is axially spaced apart from reference Bragg grating 20 a desired distance (e.g., 5 inches). Reference Bragg grating 20 and Bragg grating 22 operate on two different wavelengths so that each can be detected by light detection unit 14. A soluble layer 24 is positioned over protective coating 16 at the position of Bragg grating 22, thus effectively covering Bragg grating 22. As will be discussed in more detail below, soluble coating 24 is a strain-inducing coating that, in response to the strain induced by the coating, alters the optical response of Bragg grating 22.

The strain may be induced by soluble coating 24 in a number of ways. For example, cable 12 may be stretched or compressed while soluble layer 24 is applied and allowed to solidify, thus locking in the elongation (or length reduction) of the fiber as a residual strain in the fiber. Alternatively, instead of mechanically straining fiber cable 12 prior to coating, the coating itself may be strain-inducing. For example, soluble layer 24 may start out as a liquid and shrink (or expand) upon solidifying. Alternatively, we can instead rely on the difference of coefficient of thermal expansion between the optical fiber and the soluble coating which can be applied at temperature very different from the intended in-service temperature of the sensor. During operation, reference Bragg grating 20 and Bragg grating 22 both reflect light signals (also referred to herein as "response signals") having different wavelengths, which are ultimately received and processed by light detection unit 14.

In certain illustrative embodiments, light detection unit 14 continuously monitors and/or compares the light signals generated by Bragg gratings 20,22 and their corresponding center wavelengths. As the environment surrounding fiber optic sensor 10 changes (e.g., pressure/temperature changes), the response signals of both gratings 20,22 shift but not in the same way, because of the action of the coating 24 on grating 22. Furthermore, when fiber optic sensor 10 is exposed to a degrading fluid, soluble coating 24 begins to dissolve. As it dissolves, the strain relaxes and the wavelength of the response signal of Bragg grating 22 begins to shift while the signal of reference Bragg grating remains the same or substantially the same—thereby indicating the presence of a degrading fluid. Hence, the response signal of reference Bragg grating 20 acts as a "reference" whereby the wavelength shift of the response signal of grating 22 can be identified. Since the Bragg gratings 20,22 are designed to operate on different wavelengths, even after soluble coating 24 dissolves, the response signals of both gratings can still be processed by unit 14. As such, light detection unit 14 determines the presence of the degrading fluid. After full dissolution of coating 24, it will generally be the case that grating 22 will have a response to pressure and temperature that will be similar to that of grating 20. Therefore, the full degradation of coating 24 can be determined by the fact that the measured spectral separation of the wavelengths of gratings 22 and 24 is the same as the original "as-written" FBG gratings, taking into account the small shifts in the separation that pressure and temperature introduce on any gratings that are not at the same wavelength.

The light detection units described herein may include at least one processor, a non-transitory, computer-readable storage, transceiver/network communication module, optional I/O devices, and an optional display (e.g., user interface), all interconnected via a system bus. The network communication module may be any type of communication interface such as a fiber optic interface and may communicate using a number of different communication protocols. Software instructions executable by the processor for implementing the radioactivity mapping described herein may be stored in suitable storage or some other non-transitory computer-readable medium.

Moreover, those ordinarily skilled in the art will appreciate that the disclosure may be practiced with a variety of computer-system configurations, including hand-held devices, multiprocessor systems, microprocessor-based or programmable-consumer electronics, minicomputers, mainframe computers, and the like. Any number of computer-systems and computer networks are acceptable for use with the present disclosure. The disclosure may be practiced in distributed-computing environments where tasks are performed by remote-processing devices that are linked through a communications network. In a distributed-computing environment, program modules may be located in both local and remote computer-storage media including memory storage devices. The present disclosure may therefore, be implemented in connection with various hardware, software or a combination thereof in a computer system or other processing system.

Figure 2A:
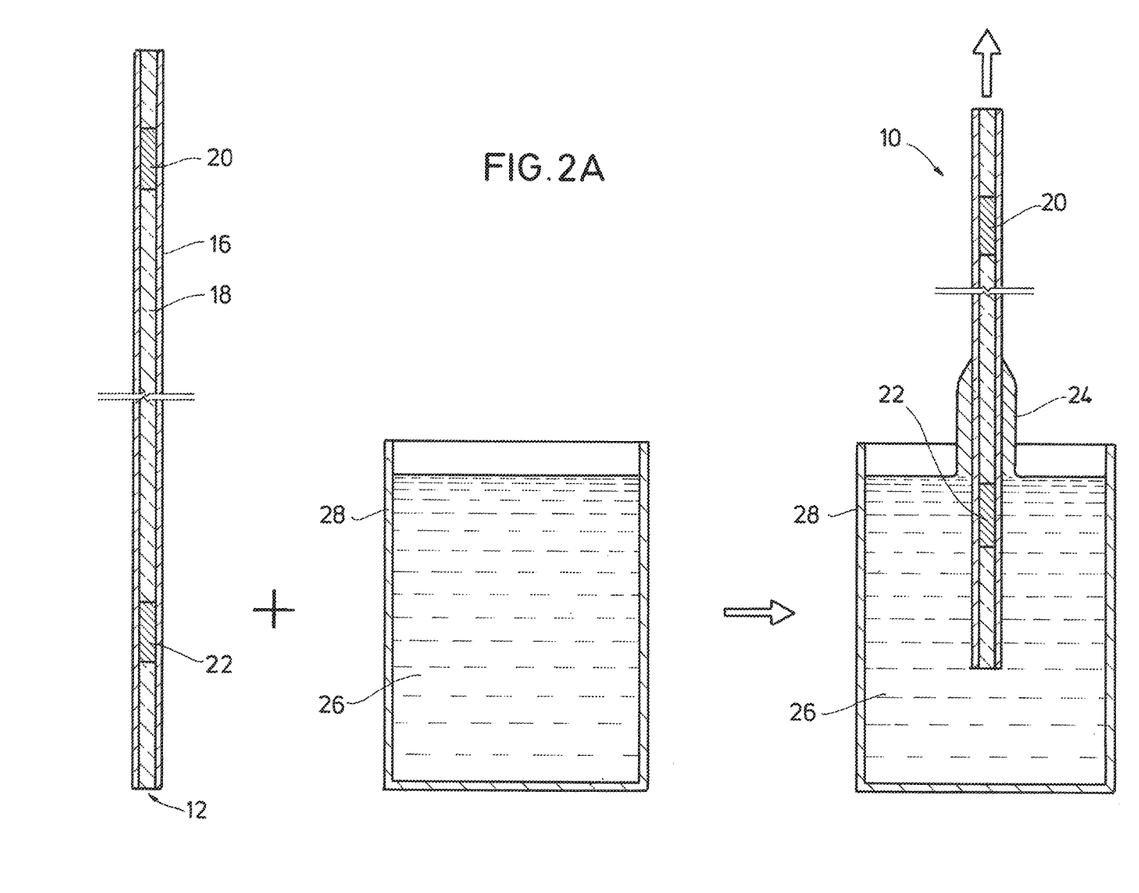
FIG. 2A depicts a dip coating method for fabricating a fiber optic sensor, according to certain illustrative methods of the present disclosure.

FIG. 2A depicts a dip coating method for fabricating a fiber optic sensor, according to certain illustrative methods of the present disclosure. In this example, soluble coating 24 is a water soluble coating of salt. Thus, in this illustrative fabrication method, fiber cable 12 is introduced to a molten salt 26 which may be placed in a container 28. The chosen soluble coating, regardless of the type, is selected such that it is solid at room temperature, but melts at a temperature less than the maximum temperature tolerated by protective coating 16. When fiber optic sensor 10 is used in a downhole application, the melting point of the soluble coating must be higher than the well temperature.

Still referring to FIG. 2A, the end of fiber cable 12 adjacent to Bragg grating 22 is then dipped into molten salt 26 as shown. In this example, fiber cable 12 is dipped into molten salt 26 and pulled back in an upward direction. As fiber cable 12 is slowly lifted, molten salt 26 adheres to the portion of protective coating 16 positioned over Bragg grating 22, effectively coating it as soluble layer 24. As the hot molten salt cools, it will contract with the temperature change which will induce a stress on cable 12. The amount of contraction will differ depending on the compound used and the temperature difference. Note, however, that other soluble coatings may be applied. Those soluble coatings may include, for example, sugars, polymers, or other organic or inorganic compounds that have the correct melting points. In other embodiments, the soluble layer may be hydrocarbon soluble, acid soluble, caustic soluble or base soluble.

Figure 2B:
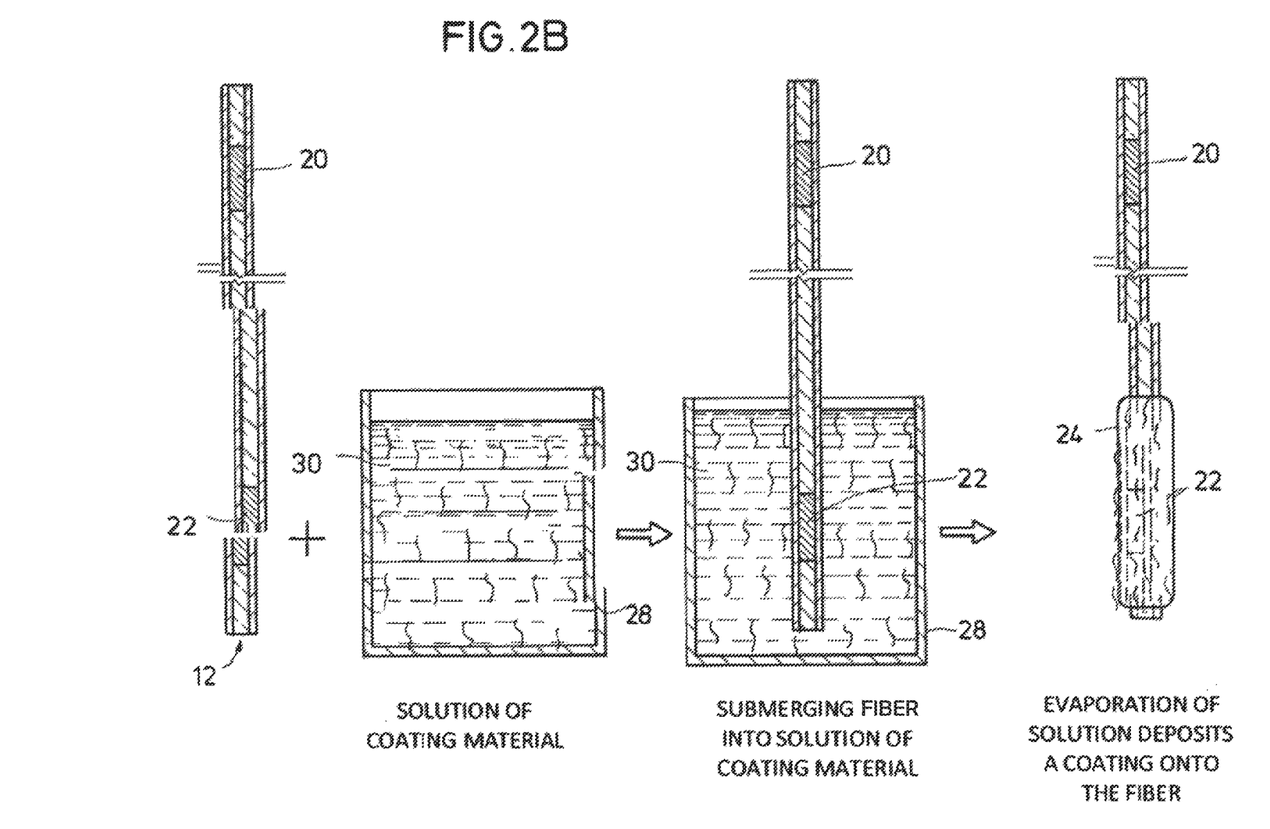
FIG. 2B depicts an alternate evaporation method for fabricating a fiber optic sensor, according to certain illustrative methods of the present disclosure.

FIG. 2B depicts an evaporation-based alternate dip-coating method for fabricating a fiber optic sensor, according to certain illustrative methods of the present disclosure. Here, fiber 12 is introduced to container 28 again, which holds a solution of soluble coating material 30 dissolved in a solvent (e.g., sugars, polymers, or other organic or inorganic compounds that have the correct solubility for the detection method). The section of fiber cable 12 adjacent Bragg grating 22 is submerged in soluble material 30 and becomes covered with the solution of coating material 30 and its solvent. Grating 22 is then pulled out of the solution and the coating 24 on grating 22 is allowed to solidify by evaporation of the solvent. This method can be defined as an evaporation-induced film deposition method. In this method, grating 22 also cools (and therefore compresses), which induces a strain on cable 12. Using this method, the melting point for the soluble coating 24 is no longer a factor. Such a method would be especially useful for coating materials with a melting point above that of protective coating 16. With the melting point restriction removed in this method, the soluble coatings available for use are numerous. For example, high melting point salts or sugars may be used.

In an alternative embodiment, a temporary protection coating may be placed over soluble layer 24. Such high-temperature coatings may include, for example, a wax material. When the optical sensors are deployed in a downhole application, the downhole environment is very hot. Thus, to sense for a particular fluid deep in the well, the high-temperature coating would protect the soluble layer until the deep location is reached by the sensor. There, the high-temperature coating would melt or otherwise dissipate, thus exposing the soluble layer to detect the desired fluid.

Beyond these fabrication methods, a variety of other techniques may be used to apply a soluble coating to the fiber cable 12. For example, spin coating, vapor deposition, painting or sputtering may be utilized. Moreover, FIGS.

1-2B illustrate fiber optic sensors having short, finite lengths, where only one end of the cable is coated. In alternate embodiments, however, the fabrication methods may be extended to applying soluble coatings to the middle of a long length fiber. Rather than submerging the fiber to be coated vertically in the coating solution, the fiber cable may be stretched horizontally across the solution or the fiber can be looped, thereby forming a "U" shape in the solution.

Moreover, as previously mentioned, the strain sensors may take a variety of forms. For example, if an alternate strain sensing method is used, such as, for example, distributed Brillouin sensing (e.g., using an OmniSense commercial Brillouin strain analyzer) may be used. Alternatively, a Rayleigh-based strain sensing technique, such as, for example, a Luna Technology OBR 4600 optical backscatter reflectometer may be used as strain sensors. These and other alterations (e.g., varying coating thickness by varying speed of withdrawal) of the methods described herein will be readily apparent to those ordinarily skilled in the art having the benefit of this disclosure.

Figure 3A:
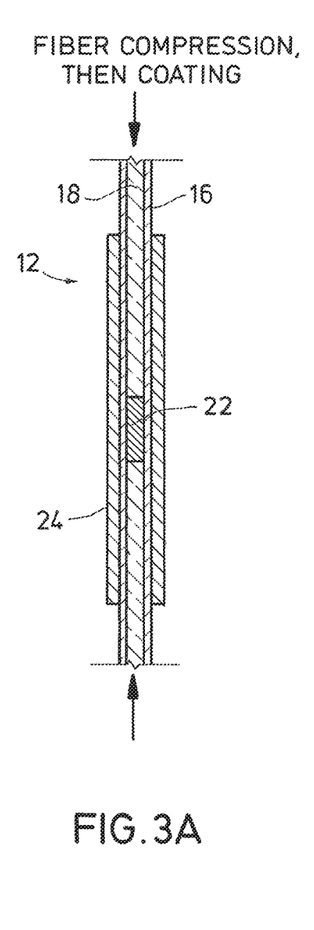
FIGS. 3A-3D illustrate yet other fabrication methods and corresponding embodiments of the present disclosure.
Figure 3B:
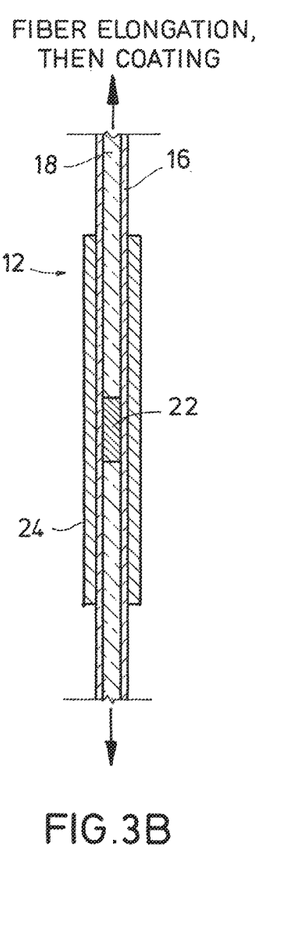

FIGS. 3A-3D illustrate yet other fabrication methods and corresponding embodiments of the present disclosure. FIG. 3A is a sectional view of a portion of a fiber optic sensor whereby fiber cable 12 is compressed while soluble layer 24 is applied; FIG. 3B is a sectional view of a portion of a fiber optic sensor whereby fiber cable 12 is stretched while soluble layer 24 is applied. The stretching and compressing of cable 12 during the coating process helps to impart even more strain on cable 12 than would be imparted by soluble layer 24 without the stretching/compression. Once soluble layer 24 cools and solidifies, it locks in the strain applied by the compression/stretching. Furthermore, by stretching/compressing cable 12 during application of soluble layer 24, a greater change in the response signal can be seen when the coating dissolves and the strain is released.

Figure 3C:
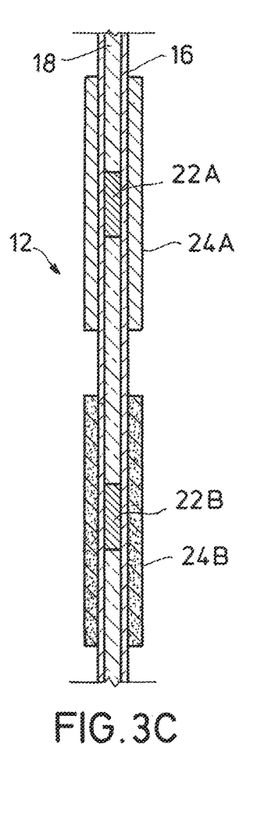

In other embodiments, multiple soluble layers may be applied along the fiber cable. FIG. 3C is a sectional depiction of a portion of another fiber optic sensor, according to certain illustrative embodiments of the present disclosure. In this embodiment, fiber optic cable 12 of this sensor is similar to those already described, as like numerals refer to like elements. However, in this illustrative embodiment, two Bragg gratings $22_A$ and $22_B$ are axially separated from one another and covered with two different soluble layers $24_A$ and $24_B$, respectively. Soluble layers $24_A$ and $24_B$ have different solubilities. For example, soluble layer $24_A$ may be water soluble, while soluble layer $24_B$ is hydrocarbon soluble. Using this embodiment, the fiber optic sensor can detect multiple degrading fluids. Alternatively, soluble layers $24_A$ and $24_B$ may both be water soluble, except they dissolve at different rates. By utilizing this embodiment, the fiber optic sensor can detect an amount of degrading fluid. Although two Bragg gratings 22 are shown along with their corresponding soluble layers 24, any number of such grating/soluble layer pairs may be placed along fiber 12 as desired and these can be combined with any number of gratings that are not covered by soluble coatings to serve as reference per the description given above.

Figure 3D:
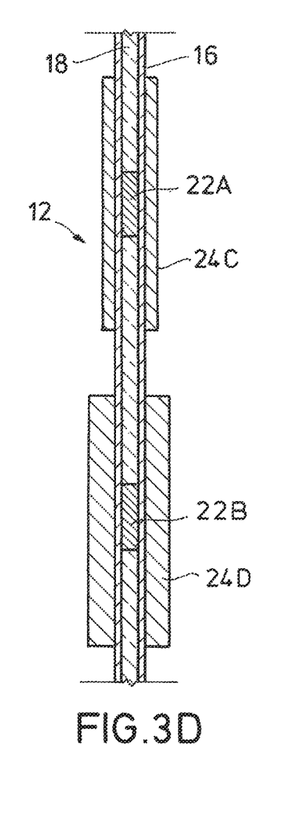

FIG. 3D is a sectional depiction of a portion of another fiber optic sensor, according to certain illustrative embodiments of the present disclosure. In this embodiment, fiber optic cable 12 of this sensor is similar to those already described, as like numerals refer to like elements. However, in this illustrative embodiment, Bragg gratings $22_A$,$22_B$ are covered by soluble layers having different thicknesses, thereby allowing detection of different exposure durations to a degrading fluid. Here, for example, soluble layers $24_C$,$24_D$ are comprised of the same material (e.g., salt), except that soluble layer $24_D$ is thicker. As a result, when the fiber optic sensor is exposed to the degrading fluid, layer $24_C$ dissolves before layer $24_D$ dissolves. As a result, through an analysis of the response signals of Bragg grating $22_A$,$22_B$ and the reference Bragg grating (not shown), the light detection unit can determine the amount/degree of the degrading fluid present in the surrounding environment. Furthermore, certain exposure thresholds can be established by the thickness of the coatings $24_C$ and $24_D$.

The fiber optic sensors described herein may be used in a variety of applications in which the presence of a degrading fluid is desired to be known. However, a downhole application will be described below in which the fiber optic sensor is deployed as part of a downhole interrogation system. In such systems, the fiber optic sensors may be deployed individually or as an array of sensors.

Figure 4A:
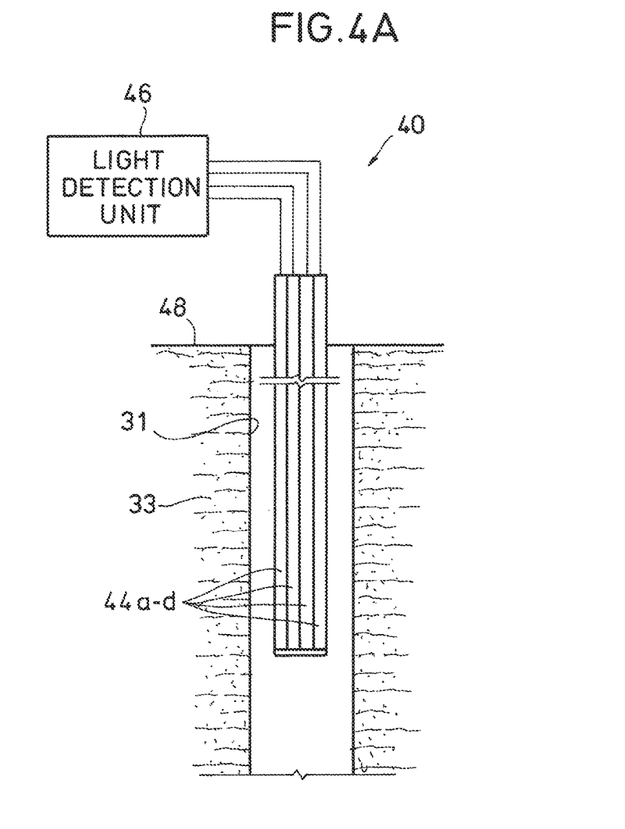
FIG. 4A is a schematic depiction of a downhole interrogation system, according to alternative illustrative embodiments of the present disclosure.

FIG. 4A is a schematic depiction of a downhole interrogation system, according to alternative illustrative embodiments of the present disclosure. As previously described, the fiber optic sensing device may be comprised of a single sensor or an array of sensors. In the illustrated embodiment, however, downhole interrogation system 40 includes an array of fiber optic sensors 44a-d. Downhole interrogation system 40 includes a light detection unit 46 positioned at a surface location 48. In other embodiments, however, light detection unit 46 may be positioned downhole. Light detection unit 46 may consist of a broadband source to illuminate the fiber and spectrometer to determine the reflected wavelengths. Alternatively, it may illuminate the fiber with a narrow band, tunable source, then wait to see which transmitted wavelengths are reflected back to the unit. Light detection unit 46 is optically coupled fiber optic sensors 44a-d. Fiber optic sensors 44a-d extend down a wellbore 31 which has been drilled in a formation 33. Light detection unit 46 is part of the signal processing chain.

In certain embodiments described herein, the light detection units are configured for positional sensitivity. In certain embodiments, this may be achieved by coupling a single light detection unit to a single fiber optic sensor, while in other embodiments a single light detection unit may be coupled to an array of fiber optic sensors, whereby the detected light photons are mapped to their respective fiber optic sensors positioned at different wavelengths in the spectral domain (wavelength-division multiplexing, e.g.).

During operation of the embodiment in FIG. 4A, light is propagated down fiber optic sensors 44a-d by light detection unit 46. As a result, with reference to the previous fiber optic sensors described herein, a reference signal having a reference wavelength is generated by Bragg grating 20. A second signal having a second wavelength, different from the reference signal wavelength, is generated by a second Bragg grating 22 having a strain induced upon it by soluble layer 24. Over the course of time, one or more of fiber optic sensors 44a-d are exposed to a degrading downhole fluid (e.g., water, hydrocarbon, acid, etc.) which degrades and/or dissolves soluble layer 24. In response to the degradation, the strain induced by soluble layer 24 is relaxed, thereby shifting the wavelength of the response signal of second Bragg grating 22 to a third signal having a third wavelength. The light detection unit 46 then receives and processes the reference, second and third signals, analyzes their respective wavelength shifts to thereby determine the presence of the degrading fluid. For example, the fluid may be determined to be a specific type of fluid (e.g., type of acid) or a class of fluids (e.g., any acid or hydrocarbon).

Light detection unit 46 may perform the fluid analysis is a variety of ways. For example, if there is both a shift in wavelength and intensity of the response signal, the analysis may involve determining the ratio of the integrated signal responses of Bragg gratings 22 and 20. When light detection unit 46 determines the ratio of responses have changed, it will be evident that soluble layer 24 has been dissolved and the degrading fluid is present. In the alternative, the fluid analysis could rely solely on Bragg grating 22, where light detection unit 46 continuously monitors the response signals for a change in intensity. In yet another analysis method, if the response signal change is solely a wavelength shift, then the analysis of light detection unit 46 would involve comparison of the response signal intensities measured at a specific wavelength or a small range of wavelengths that correspond to Bragg grating 20, coated Bragg grating 22, and dissolved coating Bragg 22. A similar approach to that above involving ratios or only monitoring Bragg grating 22 could be employed. The difference here is the need for a spectrometer versus a broad band detector. As will be readily understood by those ordinarily skilled in the art having the benefit of this disclosure, the detecting method used will determine the analysis method employed.

Nevertheless, the response signal(s) detected at light detection unit(s) 46 are converted to electrical signals and further processed to perform a number of wellbore operations. For example, the integrity of the cement layer (not shown) may be determined by the presence of water. In addition, it is undesirable to produce water from a hydrocarbon producing well. Usually hydrocarbons are produced by multiple zones and, as time goes on, water breakthrough occurs at one or more zones. Thus, the embodiments described herein may be used to determine which zones are producing water, so that production from those zones thus identified can be stopped or significantly slowed down.

Figure 4B:
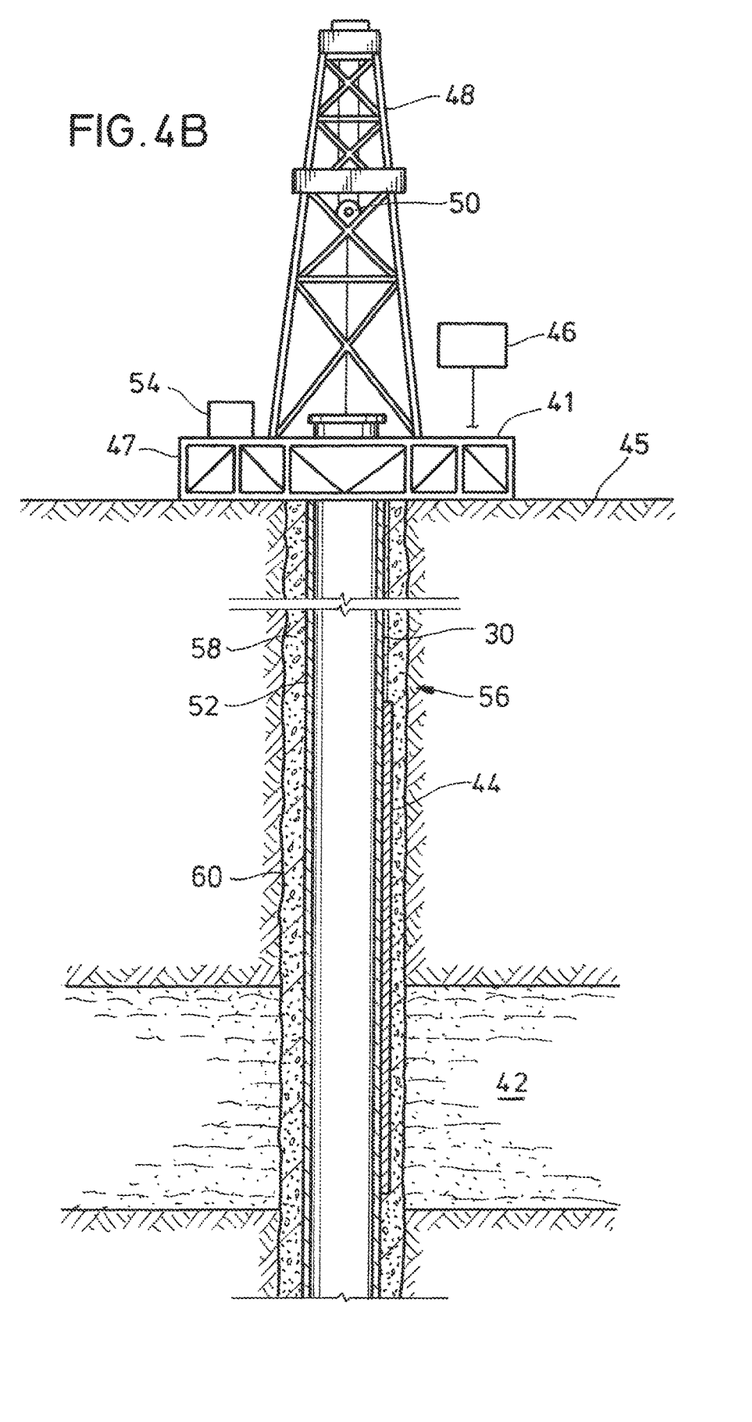
FIG. 4B is a schematic illustration of an onshore oil or gas drilling rig in which a fiber optic interrogation system has been permanently positioned along the wellbore, according to certain illustrative embodiments of the present disclosure.

FIG. 4B is a schematic illustration of an onshore oil or gas drilling rig in which a fiber optic interrogation system has been permanently positioned along the wellbore, according to certain illustrative embodiments of the present disclosure. Rig 41 is centered over a subterranean oil or gas formation 42 located below the earth's surface 45. Rig 41 includes a work deck 47 that supports derrick 48. Derrick 48 supports a hoisting apparatus 50 for raising and lowering pipe strings such as casing 52. Pump 54 is capable of pumping a variety of wellbore compositions (e.g., drilling fluid or cement) into the well and includes a pressure measurement device that provides a pressure reading at the pump discharge.

Wellbore 56 has been drilled through the various earth strata, including formation 42. Upon completion of wellbore drilling, casing 52 is placed in wellbore 56 to facilitate the production of oil and gas from formation 42. Casing 52 is a string of pipes that extends down wellbore 56, through which oil and gas will eventually be extracted. The region between casing 52 and the wall of wellbore 56 is known as the casing annulus 58. In this illustrative embodiment, a fiber optic interrogation system is utilized wherein one or more light detection unit(s) 46a-n are positioned at surface 45, while the fiber optic sensors 44a-d (along with all necessary couplings, electronics, etc.) have been permanently positioned downhole within annulus 58. In certain embodiments, fiber optic sensors 44 and a suitable optical coupler 30 may form part of casing 52. In other embodiments, they may be embedded within cement 60 used to cement casing 52 in place. In yet other embodiments, they may be positioned inside casing 52 or may form part of an inner string, such as, for example, part of a production string, or inside/outside the production string, to detect the ingress of water, for example, into the well. There are a variety of other ways in which these sensors may be permanently positioned downhole, as these are only illustrative in nature. Moreover, any of the embodiments of the fiber optic sensors described herein may be utilized in the illustrated application in FIG. 4A.

During operations of the embodiment of FIG. 4B, cement 60 may degrade over time thus exposing fiber optic sensor(s) 44 to a degrading fluid. Once exposed, the soluble layers will degrade and/or dissolve as described herein, thereby light detection unit(s) 46 will indicate the presence of the degrading fluid. In response, corrective action may be taken.

Figure 4C:
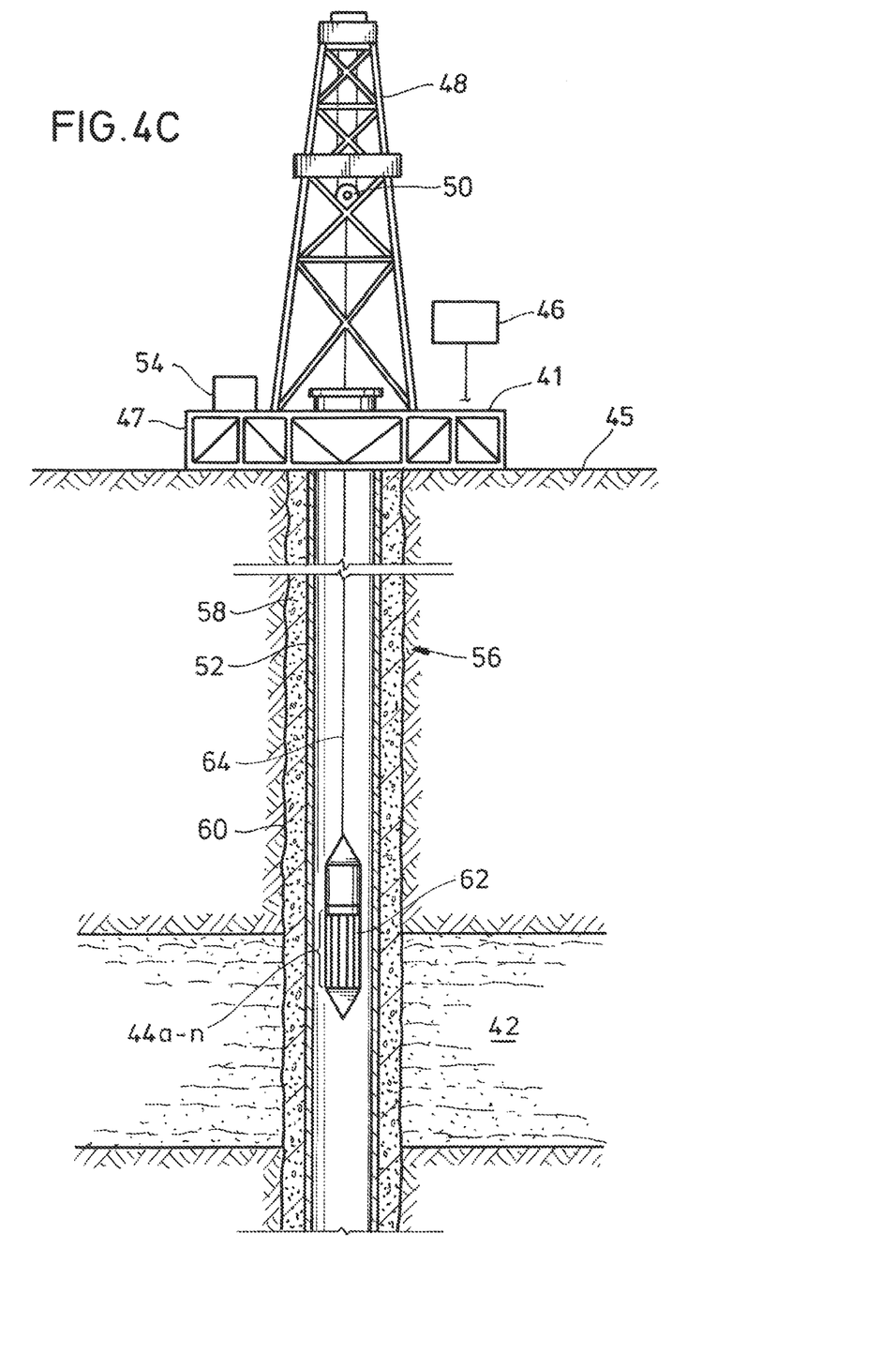
FIG. 4C illustrates yet another embodiment of the present disclosure whereby the fiber optic sensors are deployed along a wireline in a logging application.

FIG. 4C illustrates yet another embodiment of the present disclosure whereby the fiber optic sensors 44a-n are deployed along a wireline in a logging application. FIG. 4C is similar to FIG. 4B in as much as like reference numerals are used. However, the embodiment of FIG. 4C depicts a logging tool 62 being deployed along a wireline 64. Fiber optic sensors 44a-n are positioned along logging tool 62. Thus, during operation, fiber optic sensors 44a-n are deployed along wellbore 56 whereby light detection unit(s) 46 detects degrading fluids being released from formation 42 or otherwise introduced to the downhole environment.

In addition to wireline applications, the fiber optic sensors described herein may be deployed downhole in a variety of other ways including, for example, logging-while-drilling or measurement-while-drilling applications, or some other suitable downhole string.

Moreover, in addition to detecting degrading fluids, the fiber optic sensors described herein may also be used to detect temperature and pressure before the soluble layer is removed. As the temperature increases, the wavelength of the response signals will shift as well, thus indicating a temperature change.

Accordingly, the illustrative fiber optic sensors described herein may be used to interrogate hundreds or more sensing regions along the same fiber using time-division or wavelength division multiplexing, for example. They also provide a low cost approach to sensing degrading fluids in a variety of applications including, for example, downhole applications.

Embodiments and methods described herein further relate to any one or more of the following paragraphs:

1. A fiber optic sensor, comprising a fiber optic cable; a first reference strain sensor positioned within the fiber optic cable; a second strain sensor positioned within the fiber optic cable at a position axially spaced apart from the first reference strain sensor; and a soluble layer positioned over the fiber optic cable at the position of the second strain sensor.

2. A fiber optic sensor as defined in paragraph 1, wherein the soluble layer is a strain inducing layer.

3. A fiber optic sensor as defined in paragraphs 1 or 2, wherein the first reference strain sensor and the second strain sensor are Bragg gratings.

4. A fiber optic sensor as defined in any of paragraphs 1-3, further comprising a third strain sensor positioned within the fiber optic cable at a position axially spaced apart from the first reference strain sensor and the second strain sensor; and a soluble layer positioned over the fiber optic cable at the position of the third strain sensor, wherein the soluble layer of the second strain sensor has a different solubility than the soluble layer of the third strain sensor.

5. A fiber optic sensor as defined in any of paragraphs 1-4, further comprising a third strain sensor positioned within the fiber optic cable at a position axially spaced apart from the first reference strain sensor and the second strain sensor; and a soluble layer positioned over the fiber optic cable at the position of the third strain sensor, wherein the soluble layer of the second strain sensor has a different thickness than the soluble layer of the third strain sensor.

6. A fiber optic sensor as defined in any of paragraphs 1-5, wherein the fiber optic cable comprises a protective coating; and the soluble layer is positioned on the protective coating.

7. A fiber optic sensor as defined in any of paragraphs 1-6, wherein the protective coating is polyimide.

8. A fiber optic sensor as defined in any of paragraphs 1-7, wherein the soluble layer is a water, hydrocarbon, acid, caustic or base soluble layer.

9. A fiber optic sensor as defined in any of paragraphs 1-8, wherein the soluble layer is comprised of an organic compound.

10. A fiber optic sensor as defined in any of paragraphs 1-9, wherein the soluble layer is comprised of an inorganic compound.

11. A fiber optic sensor as defined in any of paragraphs 1-10 further comprising a protective coating positioned over the soluble layer.

12. A fiber optic sensor as defined in any of paragraphs 1-11, wherein the fiber optic sensor is part of a downhole interrogation system.

13. A method of fabricating a fiber optic sensor, the method comprising providing a fiber optic cable comprising a first reference strain sensor positioned within the fiber optic cable; and a second strain sensor positioned within the fiber optic cable at a position axially spaced apart from the first reference strain sensor; and applying a layer of soluble material over the fiber optic cable at the position of the second strain sensor.

14. A method as defined in paragraph 13, wherein the soluble layer is applied while the fiber optic cable is compressed.

15. A method as defined in paragraphs 13 or 14, wherein the soluble layer is applied while the fiber optic cable is stretched.

16. A method as defined in any of paragraphs 13-15, wherein the soluble layer is applied using a dip coating technique.

17. A method as defined in any of paragraphs 13-16, wherein the soluble layer is applied hot and allowed to cool, thereby inducing a strain to the fiber optic cable.

18. A method as defined in any of paragraphs 13-17, wherein the soluble layer is applied by evaporation-induced film deposition.

19. A method as defined in any of paragraphs 13-18, further comprising applying multiple soluble layers along the fiber optic cable, the soluble layers being positioned over corresponding strain sensor.

20. A method as defined in any of paragraphs 13-19, wherein the soluble layers are applied such that each has a different thickness.

21. A method as defined in any of paragraphs 13-20, wherein the soluble layers are applied such that each has a different solubility.

22. A method as defined in any of paragraphs 13-21, wherein the soluble layer is a water, hydrocarbon, acid, caustic or base soluble layer.

23. A method as defined in any of paragraphs 13-22, wherein a protective coating is applied over the soluble layer.

24. A method as defined in any of paragraphs 13-24, wherein the fiber optic sensor is deployed into a wellbore as part of a downhole interrogation system.

25. A fiber optic sensing method, comprising generating a reference signal having a reference wavelength using a reference strain sensor positioned within a fiber optic cable; inducing a strain on the fiber optic cable using a soluble layer positioned on the fiber optic cable, the soluble layer being positioned over the fiber optic cable at a position of a second strain sensor positioned within the fiber optic cable; generating a second signal having a second wavelength, different from the reference wavelength, using the second strain sensor; allowing fluid to flow over the fiber optic cable, thereby degrading the soluble layer; in response to the degradation, generating a third signal having a third wavelength, different from the second wavelength, using the second strain sensor; and determining a presence of the fluid using the reference, second and third signals.

26. A method as defined in paragraph 25, wherein determining the presence of the fluid comprises an analysis of a wavelength shift of the reference, second and third signals.

27. A method as defined in paragraphs 26 or 26, wherein determining the presence of the fluid comprises determining the presence of water, hydrocarbon, acid, caustic fluid or base fluid.

28. A method as defined in any of paragraphs 25-27, wherein one or more of the reference, second, and third signals are used to detect temperature.

29. A method as defined in any of paragraphs 25-28, wherein one or more of the reference, second, and third signals are used to detect pressure.

30. A method as defined in any of paragraphs 25-29, wherein the method is applied to interrogate a wellbore.

31. A fiber optic sensing method, comprising generating first signals using a fiber optic cable having a portion thereof coated with a soluble layer; exposing the fiber optic cable to fluid, thereby degrading the soluble layer; in response to the degradation, generating second signals; and determining a presence of the fluid using the first and second signals.

32. A method as defined in paragraph 31, wherein the first and second signals are generated using a plurality of strain sensor positioned within the fiber optic cable, the water soluble layer being positioned over at least one of the strain sensor.

33. A method as defined in paragraphs 31 and 32, wherein a degree of fluid presence is determined using a plurality of soluble layers positioned along the fiber optic cable.

34. A method as defined in any of paragraphs 31-33, wherein determining the presence of the fluid comprises an analysis of a wavelength shift of the first and second signals.

35. A method as defined in any of paragraphs 31-34, wherein determining the presence of the fluid comprises determining the presence of water, hydrocarbon, acid, caustic fluid or base fluid.

36. A method as defined in any of paragraphs 31-35, wherein the method is applied to interrogate a wellbore.

Although various embodiments and methods have been shown and described, the disclosure is not limited to such embodiments and methods and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A fiber optic sensor, comprising:
a fiber optic cable;
a first reference strain sensor positioned within the fiber optic cable;

a second strain sensor positioned within the fiber optic cable at a position axially spaced apart from the first reference strain sensor; and a water or hydrocarbon soluble layer positioned over the fiber optic cable at the position of the second strain sensor, wherein there is no layer positioned over the fiber optic cable at the position of the first reference strain sensor.

2. A fiber optic sensor as defined in claim 1, wherein the soluble layer is a strain inducing layer.

3. A fiber optic sensor as defined in claim 1, wherein the first reference strain sensor and the second strain sensor are Bragg gratings.

4. A fiber optic sensor as defined in claim 1, further comprising:

a third strain sensor positioned within the fiber optic cable at a position axially spaced apart from the first reference strain sensor and the second strain sensor; and a water or hydrocarbon soluble layer positioned over the fiber optic cable at the position of the third strain sensor, wherein the soluble layer of the second strain sensor has a different solubility than the soluble layer of the third strain sensor.

5. A fiber optic sensor as defined in claim 1, further comprising:

a third strain sensor positioned within the fiber optic cable at a position axially spaced apart from the first reference strain sensor and the second strain sensor; and a soluble layer positioned over the fiber optic cable at the position of the third strain sensor, wherein the water or hydrocarbon soluble layer of the second strain sensor has a different thickness than the soluble layer of the third strain sensor.

6. A fiber optic sensor as defined in claim 1, wherein:
the fiber optic cable comprises a protective coating; and
the water or hydrocarbon soluble layer is positioned on the protective coating.

7. A fiber optic sensor as defined in claim 6, wherein the protective coating is polyimide.

8. A fiber optic sensor as defined in claim 1, wherein the water or hydrocarbon soluble layer is comprised of an organic compound.

9. A fiber optic sensor as defined in claim 1, wherein the water or hydrocarbon soluble layer is comprised of an inorganic compound.

10. A fiber optic sensor as defined in claim 1, further comprising a protective coating positioned over the water or hydrocarbon soluble layer.

11. A fiber optic sensor as defined in claim 1, wherein the fiber optic sensor is part of a downhole interrogation system.

12. A method of fabricating a fiber optic sensor, the method comprising:

providing a fiber optic cable comprising:
a first reference strain sensor positioned within the fiber optic cable; and
a second strain sensor positioned within the fiber optic cable at a position axially spaced apart from the first reference strain sensor; and applying a layer of water or hydrocarbon soluble material over the fiber optic cable at the position of the second strain sensor, wherein there is no layer positioned over the fiber optic cable at the position of the first reference strain sensor.

13. A method as defined in claim 12, wherein the water or hydrocarbon soluble layer is applied while the fiber optic cable is compressed.

14. A method as defined in claim 12, wherein the water or hydrocarbon soluble layer is applied while the fiber optic cable is stretched.

15. A method as defined in claim 12, wherein the water or hydrocarbon soluble layer is applied hot and allowed to cool, thereby inducing a strain to the fiber optic cable.

16. A method as defined in claim 12, further comprising applying multiple water or hydrocarbon soluble layers along the fiber optic cable, the water or hydrocarbon soluble layers being positioned over corresponding strain sensor.

17. A method as defined in claim 16, wherein the water or hydrocarbon soluble layers are applied such that each has a different thickness.

18. A method as defined in claim 16, wherein the water or hydrocarbon soluble layers are applied such that each has a different solubility.

19. A method as defined in claim 12, wherein a protective coating is applied over the water or hydrocarbon soluble layer.

20. A method as defined in claim 12, wherein the fiber optic sensor is deployed into a wellbore as part of a downhole interrogation system.

21. A fiber optic sensing method, comprising:
generating a reference signal having a reference wavelength using a reference strain sensor positioned within a fiber optic cable;

inducing a strain on the fiber optic cable using a water or hydrocarbon soluble layer positioned on the fiber optic cable, the water or hydrocarbon soluble layer being positioned over the fiber optic cable at a position of a second strain sensor positioned within the fiber optic cable, wherein there is no layer positioned over the fiber optic cable at a position of the reference strain sensor;

generating a second signal having a second wavelength, different from the reference wavelength, using the second strain sensor;

allowing fluid to flow over the fiber optic cable, thereby dissolving the water or hydrocarbon soluble layer;

in response to the dissolution, generating a third signal having a third wavelength, different from the second wavelength, using the second strain sensor; and determining a presence of water or hydrocarbon in the fluid using the reference, second and third signals.

22. A method as defined in claim 21, wherein determining the presence of the fluid comprises an analysis of a wavelength shift of the reference, second and third signals.

23. A method as defined in claim 21, wherein one or more of the reference, second, and third signals are used to detect temperature.

24. A method as defined in claim 21, wherein one or more of the reference, second, and third signals are used to detect pressure.

25. A method as defined in claim 21, wherein the method is applied to interrogate a wellbore.

26. A fiber optic sensing method, comprising:
generating a first signal using a fiber optic cable having a portion thereof coated with a water or hydrocarbon soluble layer;

exposing the fiber optic cable to fluid, thereby dissolving the water or hydrocarbon soluble layer;

in response to the dissolving, generating a second signal using the portion of the fiber optic cable coated with the water or hydrocarbon soluble layer;

generating a third signal using a portion of the fiber optic cable that is not coated with a layer; and determining a presence of water or hydrocarbon in the fluid using the first, second, and third signals.

27. A method as defined in claim 26, wherein the first and second signals are generated using a plurality of strain sensors positioned within the fiber optic cable, the water or hydrocarbon soluble layer being positioned over at least one of the strain sensors.

28. A method as defined in claim 26, wherein a degree of fluid presence is determined using a plurality of water or hydrocarbon soluble layers positioned along the fiber optic cable.

29. A method as defined in claim 26, wherein determining the presence of the fluid comprises an analysis of a wavelength shift of the first and second signals.

30. A method as defined in claim 26, wherein the method is applied to interrogate a wellbore.

31. A fiber optic sensor as defined in claim 1, wherein:
the first reference strain sensor operates on a first wavelength and the second strain sensor operates on a second wavelength different from the first wavelength; and
the fiber optic sensor further comprises a light detection unit coupled to the fiber optic cable to perform operations comprising:
generating a reference signal having the first wavelength using the first reference strain sensor;
inducing a strain on the fiber optic cable using the soluble layer positioned over the fiber optic cable at the position of the second strain sensor;
generating a second signal having the second wavelength using the second strain sensor;
allowing fluid to flow over the fiber optic cable, thereby dissolving the water or hydrocarbon soluble layer;
in response to the dissolution, generating a third signal having a third wavelength different from the second wavelength, using the second strain sensor; and
determining a presence of water or hydrocarbon in the fluid using the reference signal, second signal, and third signal.

* * * * *